US011744854B2

(12) United States Patent
Kijima

(10) Patent No.: US 11,744,854 B2
(45) Date of Patent: Sep. 5, 2023

(54) COMPOSITION COMPRISING NATURAL EXTRACTS AND AN IRON SALT

(71) Applicants: Yoshishima Kijima, Tokyo (JP); Mamdooh Helal Ghoneum, Los Angeles, CA (US)

(72) Inventor: Yoshimasa Kijima, Toyko (JP)

(73) Assignees: Yoshimasa Kijima, Tokyo (JP); Mandooh Helal Ghoneum, Los Angeles, CA (US)

( * ) Notice: Subject to any disclaimer, the term of this patent is extended or adjusted under 35 U.S.C. 154(b) by 276 days.

(21) Appl. No.: 17/095,349

(22) Filed: Nov. 11, 2020

(65) Prior Publication Data

US 2021/0145868 A1 May 20, 2021

(30) Foreign Application Priority Data

Nov. 19, 2019 (JP) .................................. 2019-208856

(51) Int. Cl.
| | |
|---|---|
| *A61K 33/30* | (2006.01) |
| *A61K 33/26* | (2006.01) |
| *A61K 31/58* | (2006.01) |
| *A61K 36/07* | (2006.01) |
| *A61K 36/23* | (2006.01) |
| *A61P 25/28* | (2006.01) |

(52) U.S. Cl.
CPC .............. *A61K 33/30* (2013.01); *A61K 31/58* (2013.01); *A61K 33/26* (2013.01); *A61K 36/07* (2013.01); *A61K 36/23* (2013.01); *A61P 25/28* (2018.01)

(58) Field of Classification Search
CPC ........ A61K 33/30; A61K 31/58; A61K 33/26; A61K 36/07; A61K 36/23; A61P 25/28
See application file for complete search history.

(56) References Cited

U.S. PATENT DOCUMENTS

| 6,203,821 B1 | 3/2001 | Kijima | |
|---|---|---|---|
| 2018/0369306 A1* | 12/2018 | Cohen | ............... A23L 33/105 |

FOREIGN PATENT DOCUMENTS

| JP | 03-063593 B | 10/1991 |
|---|---|---|
| JP | 04-027171 B | 5/1992 |
| JP | 10-066982 A | 3/1998 |
| JP | H10114666 A1 | 5/1998 |
| JP | 3495712 B2 | 2/2004 |
| JP | 2007135493 A | 6/2007 |
| JP | 3225012 U | 2/2020 |

OTHER PUBLICATIONS

Rajashree. "Effect of Salacia Reticulata W. and *Clitoria ternatea* L. on the cognitive and behavioural changes in the streptozotoxin-induced young diabetic rats," J. Basic Clin Physiol Pharmacol 2017, 28(2): 107-114. (Year: 2017).*

Prasan R. Bhandari, Mohammad Ameeruddin Kamdod. "*Emblica officinalis* (Amla): A review of potential therapeutic applications," Int J Green Pharmacy, Oct.-Dec. 2012, 257-269 (Year: 2012).*

Chiu, Chuan-Sung, et al. "Diosgenin ameliorates cognition deficit and attenuates oxidative damage in senescent mice induced by D-galactose," The American Journal of Chinese Medicine 39.03 (2011): 551-563. (Year: 2011).*

Malavika Vinodkumar, Juergen G. Erhardt, S. Rajagopalan. "Impact of a Multiple-micronutrient Fortified Salt of the Nutritional Status and Memory of Schoolchildren," Int. J. Vitam. Nutr. Res. 79(5), 2009, 348-361. (Year: 2009).*

M. H Ghoneum, J. K. Gimzewski, A.D. Ghoneum, S. Agrawal. "Potential role of MRN-100, an iron-based compound, in upregulating production of cytokine IL-10 in human dendritic cells to promote an anti-inflammatory response in vitro." Int. J. Immunopathology and Pharmacology, vol. 33: 1-11, 2019. (Year: 2019).*

* cited by examiner

*Primary Examiner* — Michael P Cohen
(74) *Attorney, Agent, or Firm* — R. NEIL SUDOL; HENRY D. COLEMAN

(57) ABSTRACT

A composition which, in addition of the synergy of action of each of the composition-forming materials, can significantly enhance the efficaciousness of each material. Specifically, the composition comprises each of extract obtained from gotukora, amla, kotarahinbutsu, diosgenin and yamabushi-take, and a divalent/trivalent iron salt as effective ingredients. The efficacy of each of the composition-forming materials is even more enhanced beyond expectation by containing the divalent/trivalent iron salt.

6 Claims, 9 Drawing Sheets

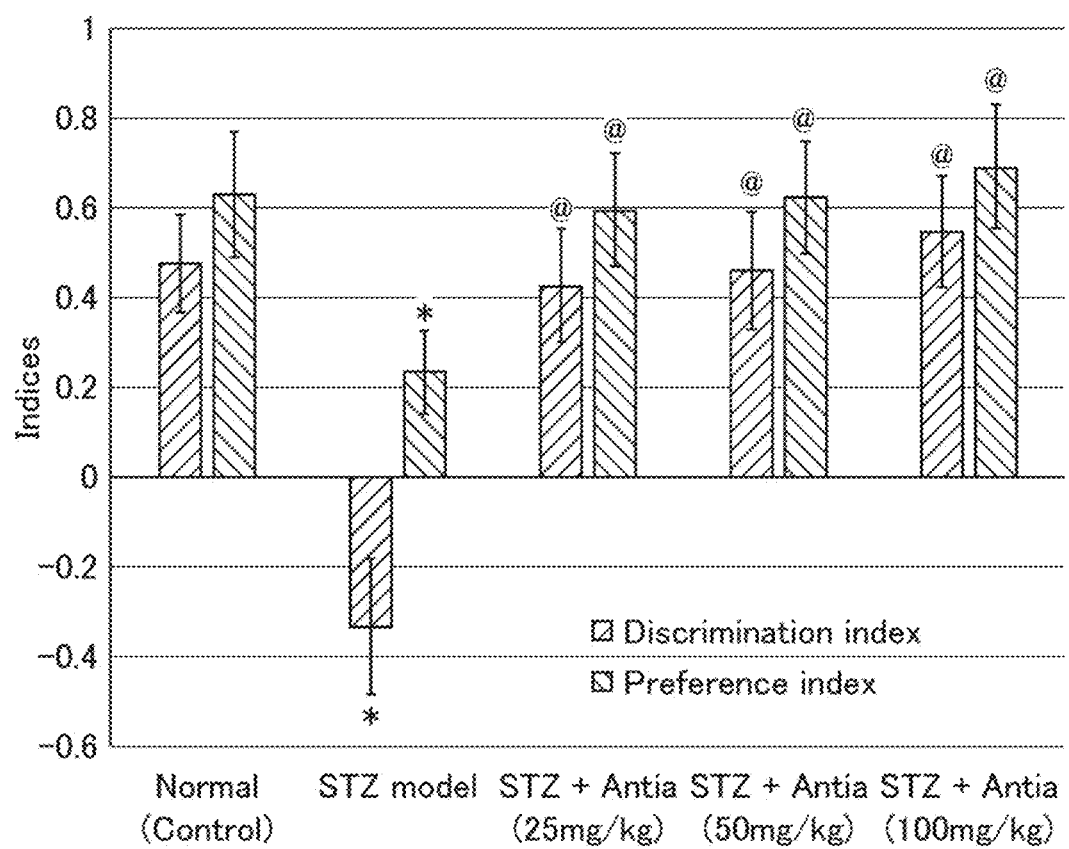

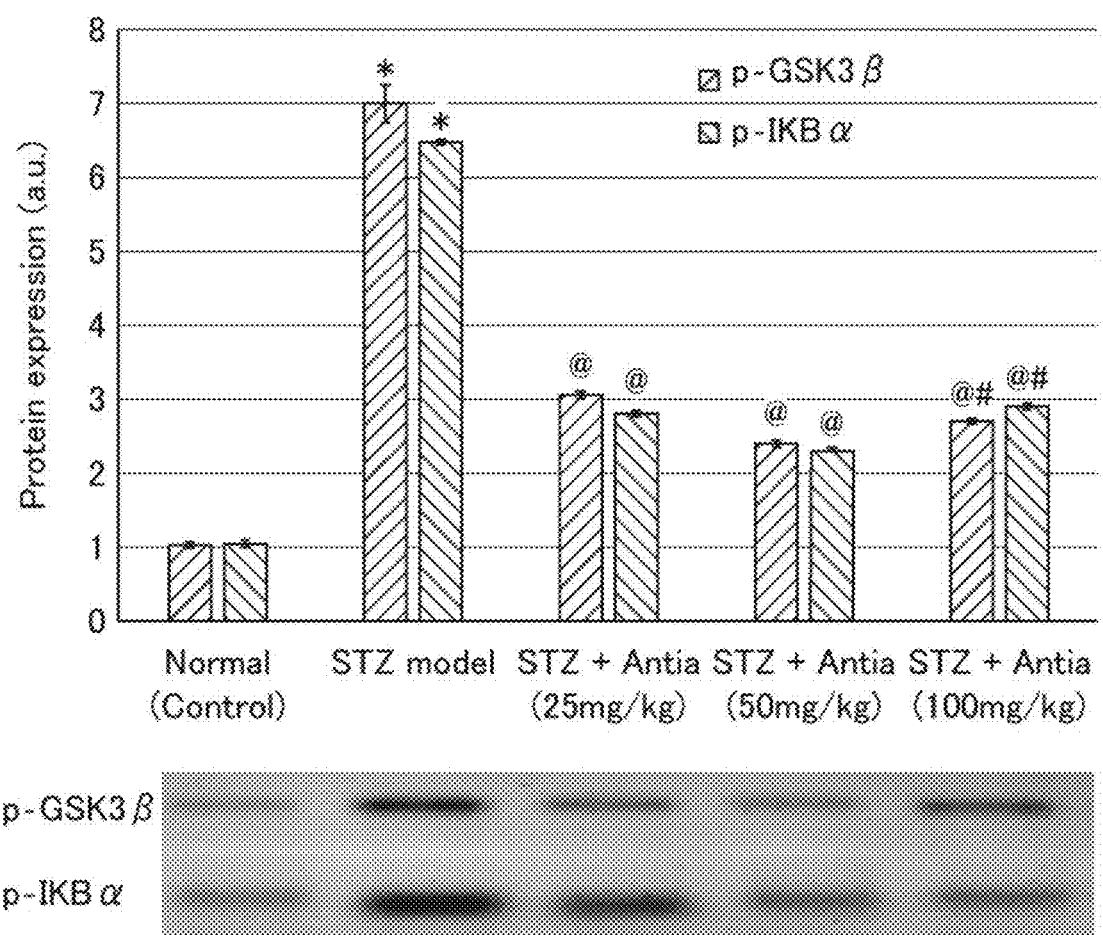

COMPOSITION COMPRISING NATURAL EXTRACTS AND AN IRON SALT

FIELD OF THE INVENTION

The present invention relates to a composition having various functions. More specifically, the invention is concerned with a composition having multiple functions or effects inclusive of, for instance, cognitive impairment prevention function, health promotion function, dietary supplement function, and cosmetic function.

BACKGROUND ART

So far, supplements (foodstuff compositions) having a cosmetic function as an example by containing collagen, gotukora (*Centella asiatica*) and deep ocean water have been put forward in the art (for instance, see Patent Publication 1).

Allegedly, the foodstuff composition (cosmetic supplement) of Patent Publication 1 uses *Centella asiatica*, deep ocean water and collagen in combination so that skin metabolism could be enhanced and skin could be kept from aging by way of the actions of the composition-forming ingredients, leading to enhanced cosmetic effects.

A dietary supplement (health food) prepared by adding and mixing *Centella asiatica* (gotukora) to and with amla has also been proposed as a supplement (health food) having a health promotion function as an example (for instance, Patent Publication 2). According to this supplement of Patent Publication 2, the effect of an efficacious ingredient of amla could be enhanced by the synergy of amla and *Centella asiatica* (gotukora) thereby making improvements in the health promotion effect.

On the other hand, the present inventor has invented and proposed an active water containing divalent/trivalent iron salt and an organogermanium compound in water as a novel active water having pharmaceutical and physiological actions (Patent Publication 3) as well as a refreshment containing a divalent/trivalent iron salt and an organogermanium compound and further containing royal jerry and/or propolis as a novel refreshment capable of making its pharmaceutical and physiological actions much higher than those of the active water (Patent Publication 5).

In this connection, it is noted that the former "active water" has already been patented in America by having regard to its efficacy (Patent Publication 5).

PRIOR ARTS

Patent Publications

Patent Publication 1: Japanese Patent No. 3495712
Patent Publication 2: JP(A) 2007-135493
Patent Publication 3: JP(A) 10-66982
Patent Publication 4: JP(A) 10-114666
Patent Publication 5: U.S. Pat. No. 6,203,821

DISCLOSURE OF THE INVENTION

According to Patent Publications 1 and 2, it is possible to obtain a supplement having its respective properties (a food composition according to Patent Publication 1 and a health food according to Patent Publication 2).

However, Patent Publication 1 makes use of the synergy (effect) of the actions the ingredients: *Centella asiatica* (gotukora), deep ocean water and collagen have from the first. Patent Publication 2 also makes use of the synergy of the actions the respective ingredients: amla and *Centella asiatica* (gotukora) have from the first. For this reason, it is not expectable to improve the effect of each ingredient.

Given such situations as stated above, the present invention has for its object to provide a composition having untold functions (efficacies) by relying on the respective materials (ingredients) forming the composition and taking advantage of the outcomes of further research and development by the inventor.

The inventor has kept on doing studies and experiments to attain the aforesaid object, and consequently found that it is achieved by the invention disclosed herein.

That is, one aspect of the invention relates to a composition characterized by containing each of extracts from gotukora, kotarahinbutsu, diosgenin and yamabushitake, and a divalent/trivalent iron salt as effective ingredients.

Another aspect of the invention relates to a composition according to the first aspect, characterized in that the composition is used for prevention and/or treatment of cognitive impairment.

Yet another aspect of the invention relates to a composition according to the first or second aspect, characterized by further containing zinc as an effective ingredient.

Each of the compositions according to one embodiment of the invention will now be explained in greater details.

The divalent/trivalent iron salt—a recently developed active substance—would appear to be a single compound having a nature halfway between those of divalent iron and trivalent iron or a single compound in which divalent iron and trivalent iron coexist. This divalent/trivalent iron salt is now capable of industrial production (for instance, see Japanese examined published application Nos. 3-63593 and 4-27171).

For instance, the divalent/trivalent iron salt may be exemplified by a compound having the following formula:

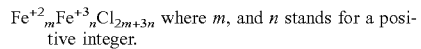

$Fe^{+2}{}_m Fe^{+3}{}_n Cl_{2m+3n}$ where $m$, and $n$ stands for a positive integer.

The divalent/trivalent iron salt may be obtained in a transition form or state by way of valence transformation where ferric chloride as an example is introduced into an aqueous solution of a strong alkali such as sodium hydroxide, calcium hydroxide, potassium hydroxide or lithium hydroxide (first approach). For instance, the first approach is exemplified by a specific process comprising the following steps: a step of dissolving ferric chloride in an aqueous solution of a strong alkali, a step of neutralizing the resultant solution, and a step of concentrating the neutralized solution.

The divalent/trivalent iron salt may also be obtained in a solution form in which a trivalent iron salt is mixed with a divalent metal salt. Specifically, the iron salt is obtained by adding and dissolving a ferric salt to and in a dilute aqueous solution containing, for example, a trivalent iron salt and a divalent metal salt at a given concentration, and concentrating the obtained solution (second approach). For instance, the divalent iron salt used herein includes ferric chloride, ferric sulfate, and ferric nitrate, and the divalent metal salt used herein includes calcium chloride, magnesium chloride, zinc chloride, magnesium sulfate, calcium sulfate, magnesium nitrate, and zinc nitrate.

The ratio m:n in the formula of the divalent/trivalent iron salt may have a specific value depending on the type of substances used for the production of the aforesaid compound, etc.

The divalent/trivalent iron salt makes significant enhancements in the actions (efficacies) of the composition-forming substances inclusive of gotukola (*Centella asiatica*). Thus, if the composition-forming substances inclusive of gotukola are mixed with an oily mixed solution as an example and the divalent/trivalent iron salt is added to and mixed with the resulting mixture, it is then possible to enhance the functions (actions) that the respective substances have. The divalent/trivalent iron salt is found to be effective even in very small amounts. This outcome has been confirmed by the inventor's experimentation. The composition according to the present invention may typically be used as an oral medicine.

Gotukola also called "gotukula" is a herb known as *Centella asiatica* in Japan.

In Indian traditional medicine "ayurveda", gotukola (*Centella asiatica*) has been used from old as a drug for treatment of sores caused by infectious diseases like Hansen's disease, and ulcerations. In addition, it is used in various applications for the purpose of blood circulation promotion, blood purification, immunity promotion, intelligence improvements and memory enhancements. It has been confirmed that gotukola is composed of triterpens such as madecassoide, asiaticoside, asiatic acid and madecassic acid, and savonigens. Eaten as leafy vegetables in Bangladesh, Thailand and Sri Lanka, gotukola (*Centella asiatica*) would not appear to give rise to any problem in terms of safety.

Amla having a botanical name of *Pbyllanthus emblica* is a deciduous shrub or small tree of the family Phyllanthaceae, which is also called "Indian gooseberry", and called amlaki in Sanskrit, which stands for a nurse.

Amla is efficacious for preventing diabetes and high blood pressure, reducing cholesterol counts, enhancing skin, relieving constipation, preventing anemia, enhancing resistance to stresses, preventing white hair and loss of hair, and so on.

Kotarahinbutsu having a botanical name of *Salacia reticulata* is a liana of the order Salacia, the family Celastrale and the genus *Celastraseae*, is efficacious for prevention of diabetes, and is used as a drug for treatment of diabetes in India, Ayurveda with its effect acknowledged by WHO in 2002.

Diosgenin is a natural ingredient contained in yam; it has been used from old as a natural drug efficacious for nutritional enhancement and known to have various efficacies such as anticancer effect, improvements in food allergy, anti-aging effect and diet effect.

Yamabushitake having a botanical name of *Hericium erinaceus* is a sort of edible mushrooms that belongs to the family *Hericium coralloides*, the genus *Hericium coralloides* and now attracts attention for dementia treatment. The ingredient "helicenone" contained in Yamabushitake has recently attracted attention as a specific against dementia. In addition, it is expected that helicenone will potentially have effects on infectious diseases, circulatory organs, digestive organs, internal incretion, and so on.

Zinc is a sort of the 16 minerals essential to the human body; zinc acts to keep the sense of taste normal, activate an antioxidant action, enhance immune force, and support development and growth. Additionally, it is expected to keep skin or hair clean and throw off depression.

Advantages of the Invention

According to the invention, it is possible to provide a composition capable of inducing the synergy of the actions of the composition-forming substances, inclusive of gotukola (*Centella asiatica*), and enhancing the function (efficacy) of each substance itself beyond expectation.

BRIEF EXPLANATION OF THE DRAWINGS

FIGS. 2A, 2B and 2C show the results of testing (1), in which FIG. 2A shows an effect of Antia on mean escape latency (MEL) in Morris water maze, FIG. 2B shows an effect of Antia on time spent in target quadrant in Morris water maze, and FIG. 2C shows an effect of Antia on cognitive function in the novel object recognition test for ICV-STZ injected mice, and in which symbol * significantly different from normal group at $p<0.05$, and symbol @ significantly different from ICV-STZ group at $p<0.05$.

FIGS. 6A to 6D show the results of testing (5), in which FIG. 6A indicates an effect of Antia on protein expression in the hippocampi of ICV-STZ injected mice for (A) phosphorylated STAT and JAK, FIG. 6B indicates an effect of Antia on protein expression in the hippocampi of ICV-STZ injected mice for GSK3β and IKBα, FIG. 6C indicates an effect of Antia on protein expression in the hippocampi of ICV-STZ injected mice for mTOR and p-AKT, and FIG. 6D indicates an effect of Antia on protein expression in the hippocampi of ICV-STZ injected mice for COX-2, respectively, in which symbol * significantly different from normal group at $p<0.05$, symbol @ significantly different from ICV-STZ group at $p<0.05$, symbol # significantly different from Antia (25 mg/kg) at $p<0.05$, and symbol $ significantly different from Antia (50 mg/kg) at $p<0.05$.

DESCRIPTION OF EMBODIMENTS

Figure 1:
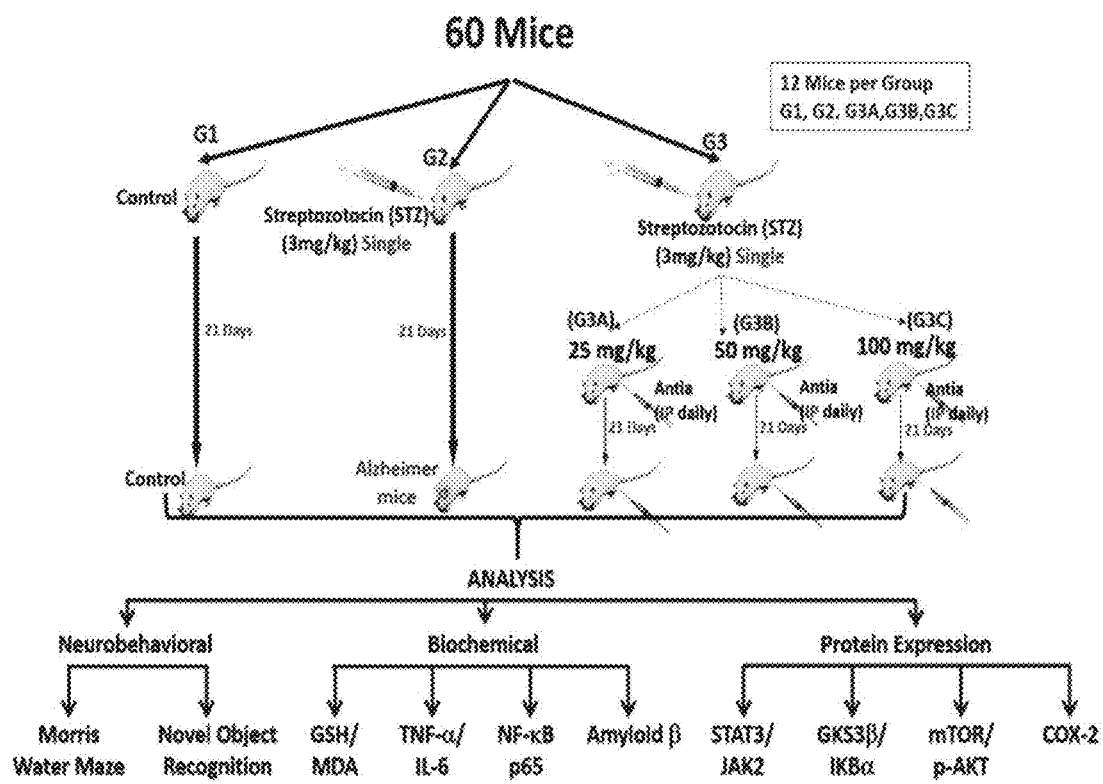
FIG. 1 is illustrative of how to carry out testing according to one embodiment of the invention.

One embodiment of the composition according to the invention is now explained with reference to the accompanying drawings.

The composition according to this embodiment is composed of substances (ingredients): extracts from gotugola, amla, kotarahinbutsu, diosgenin (yam extract), yamabushitake and a divalent/trivalent iron salt (MRN-100).

The composition (Antia) of the instant embodiment may be produced as by forming the starting substances (ingredients) inclusive of gotukola and amla in a powder-and-particle, powdery or granular form and then formulating them in a desired manner.

Although there is no limitation to the blending ratio of the starting ingredients, for instance, the divalent/trivalent iron salt (MRN-100), gotukola, amla, kotarahinbutsu, diosgenin and yamabushitake may be used in amounts of about 1.5 to about 4.0% by weight, about 20.0 to about 28.0% by weight, about 13.0 to about 18.0% by weight, about 20.0 to about 26.0% by weight, about 20.0 to about 26.0% by weight and about 10.0 to about 15.0% by weight per the total composition, respectively.

It is here noted that the starting substances (ingredients) of the composition may be mixed and added with a very small amount of zinc as desired. Although there is no particular limitation to the blending ratio of zinc, for instance, zinc may be used in an amount of about 0.5 to about 1.5% by weight per the total composition.

Examples

Referring then to some examples of the invention, the following is given as an example to which, of course, the invention is not limited.

The divalent/trivalent iron salt (MRN-100) used in the following example was prepared as described below.

Ferric chloride (1.0 mg) was placed, stirred and dissolved in 100 ml of a 0.5 N caustic soda aqueous solution, and then let standing for 24 hours. Insoluble matter occurring in the resultant solution was removed, and the solution was neutralized with hydrochloric acid. Then, the solution was concentrated under reduced pressure and dried in a desiccator for crystallization. An 80% by weight aqueous solution of isopropyl alcohol (50 ml) was added to the obtained crystal for re-dissolution, and concentrated under reduced pressure for removal of the solvent, followed by drying. This re-dissolution/concentration/drying cycle was repeated several times to obtain a crystal in an amount of 0.25 mg. This crystal was dissolved in water (distilled water or pure water) to obtain an aqueous solution diluted about 100 times to about 10,000 times, viz., an aqueous solution containing the divalent/trivalent iron salt in an amount of about 0.01% to about 1% (a source liquid for the divalent/trivalent iron salt). This source liquid is powdered into the divalent/trivalent iron salt that was then used herein.

In this example, compositions (Antia) prepared from material Nos. 1 to 6 (in a powder-and-particle state) in amounts set forth in the following table were used as sample compositions.

TABLE 1

| | Name of the Raw Materials | Amounts |
| --- | --- | --- |
| No. 1 | Gotukora | 23.25% by weight |
| No. 2 | Amla | 15.0% by weight |
| No. 3 | Kotarahinbutsu | 23.0% by weight |
| No. 4 | Diosgenin | 23.0% by weight |
| No. 5 | Yamabushitake | 12.25% by weight |
| No. 6 | Divalent/Trivalent Iron Salt | 3.5% by weight |

Given below is the gist of the examples where the aforesaid samples are used.

It is here noted that Antia (an antioxidant comprising MRN-100 (a divalent/trivalent iron salt) blended in extracts obtained from edible yamabushitake, gotukora, kotrahinbutsu plant, diosgenin (an extract from yam tuber) and amla (Indian gooseberry).

INTRODUCTION

Age-related neurological disorders such as Alzheimer's disease (AD) are on the rise. AD is a neurodegenerative disorder characterized by a progressive decline of memory and cognition, and it is the most common cause of dementia, accounting for 60-80% of all cases. The most common type of AD in the elderly, sporadic Alzheimer's disease (SAD), is associated with progressive neurodegeneration of the central nervous system. Several pathways have been examined as possible targets for SAD, including the oxidative stress, amyloidogenic, inflammatory, and autophagy pathways.

The appearance of oxidative stress markers is one of the earliest changes in AD brains, preceding the accumulation of visible amyloid deposits and neurofibrillary tangles. Oxidative stress is implicated in many disorders like chronic inflammation, AD, and Parkinson's disease. Neurons in the brain are at extremely high risk of excessive generation of reactive oxygen species (ROS) and oxidative damage since they show high oxygen consumption and energy production.

In AD brains, normally solid amyloid-β (Aβ) and tau proteins assemble into amyloid-like filaments called plaques and tangles. It is currently unresolved how Aβ accumulates in the central nervous system and initiates cell disease, but a suggested mechanism by which Aβ may damage neurons and cause neuronal death includes ROS generation during Aβ self-aggregation. When this occurs on the membrane of neurons in vitro, it ultimately leads to depolarization of the synaptic membrane, excessive calcium influx, and mitochondrial impairment.

Neurodegenerative diseases such as AD are also accompanied by neuroinflammation. The transcription factor NF-κB has been found to play a crucial role in the inflammatory response of neurons. Under normal physiological conditions, NF-κB forms a cytoplasmic complex with its inhibitor IκBα as an inactive form, but when stimulated, NF-κB can induce the transcription of inflammatory target genes such as cyclooxygenase-2 (COX-2), interleukin-1β (IL-1β), interleukin-6 (IL-6), and tumor necrosis factor-α (TNF-α). In addition, neuroinflammation has been linked with autophagy in neurodegenerative diseases. Pathological disruption of autophagy can cause an initiation or exacerbation of neuroinflammation and, conversely, neuroinflammation can induce an autophagic deficit that exacerbates neurodegeneration. In human AD, as well as in mouse models of AD, autophagy has been found to be decreased and to contribute to the pathological accumulation of tau aggregates. Autophagy is known to be regulated by mTOR, the mammalian target of rapamycin, and mTOR inhibition has been shown to prevent neuroinflammation in a mouse model of cerebral palsy. Moreover, it has been demonstrated that GSK-3β inhibition suppresses neuroinflammation in the cortices of rats subjected to ischemic brain injury by activating autophagy.

Pharmacological management of AD has been limited to date. Long-term usage of non-steroidal anti-inflammatory drugs (NSAIDs) were thought in 2007 to be associated with a reduced likelihood of developing AD. Evidence also suggested the notion that NSAIDs could reduce inflammation related to amyloid plaques, but trials were suspended due to high adverse events. There are no medications or supplements that have been shown to decrease risk of AD, and unfortunately, current FDA-approved AD treatments only offer symptomatic relief and are unable to delay or cure the disease.

Recently, antioxidants have received increased attention in preventing the onset of AD by reducing oxidative stress insult. Furthermore, the use of and search for drugs and dietary supplements from plants have accelerated in recent years, due in part to the health benefits that have been found in phytochemicals whose uses have been documented in traditional medicine. Components of the traditional Chinese medicinal mushroom called yamabushitake promote nerve growth factor synthesis in cultured astrocytes as well as improving mild cognitive impairment in humans. The gotsukora plant has traditionally been used for dementia and memory improvement, and its extracts have been shown to improve memory retention in rodents, alter amyloid beta pathology in the hippocampus of a mouse model of AD, and modulate the oxidative stress response implicated in neurodegenerative changes that occur with AD. Diosgenin, a plant-derived steroidal sapogenin, has been shown to exert anti-cancer effects, improve aging-related cognitive deficits, and relieve diabetic neuropathy. Recently, it was proven that diosgenin improves memory function and reduces axonal degeneration in AD mouse models. Amla, the Indian gooseberry, has been shown to have potent radical scavenging effects; to have a high degree of neuro-protective potential in a panel of bioassays that targeted oxidative stress, carbonyl stress, protein glycation, Aβ fibrillation, acetylcholinesterase inhibition, and neuroinflammation; and to improve the cognitive functions, brain antioxidant enzymes, and acetylcholinesterase activity in a rat model of AD. Finally, kothala himbutu (*Salacia reticulata*) has been shown to protect against deleterious cognitive changes in streptozotocin-induced young diabetic rats and against mercury toxicity in mice hippocampi.

In this study, we examine the cogno-protective effects of an anti-oxidant product called Antia whose components include yamabushitake, gotsukora, diosgenin, amla, and kothala himbutu. These components are treated together with the hydroferrate fluid MRN-100 to generate Antia. Previous research on MRN-100 has shown it to protect against age-associated oxidative stress and against oxidative damage in endothelial cells as well as in murine and human leukemia cells. Recent studies on Antia have shown its ability to reverse oxidative-stress-induced mitochondrial dysfunction in human peripheral blood lymphocytes. In light of the above-mentioned neuroprotective effects of Antia's plant components, we hypothesized that Antia would have beneficial effects on the pathways relevant to AD, namely the oxidative stress, amyloidogenic, inflammatory, and autophagy pathways. We studied the effect of Antia on mice induced with SAD via intracerebroventricular (ICV) injection of streptozotocin (STZ); this is a well-established animal model of SAD based on brain resistance to insulin and imitates the age-related pathology of SAD in humans such as memory impairment, oxidative stress, neuroinflammation, and neurodegeneration. Here we present behavioral, biochemical, and Western blot experiments in support of our hypothesis.

(Methods)
(Animals)

Adult male albino mice weighing 25-30 g were provided by the animal facility of the Faculty of Pharmacy, Cairo University, Egypt, and they were allowed to acclimate for one week before conducting the study. Animals were housed in controlled environmental conditions of constant temperature (25±2° C.), relative humidity of 60±10%, and light/dark cycle (12/12-h). Standard chow diet and water were allowed ad libitum. All efforts were utilized to minimize animal suffering and to reduce the number of animals used. This study was approved by the Ethics Committee for Animal Experimentation (Faculty of Pharmacy, Cairo University) and complied with the recommendations of the National Institutes of Health Guide for Care and Use of Laboratory Animals (2011).

(Chemicals)

STZ was purchased from Sigma-Aldrich Co. (St Louis, Mo., USA). STZ was dissolved in saline solution (0.9% NaCl) and injected ICV at a volume of 10 μL by the freehand method. Antia was dissolved in saline solution in three doses: 25 mg/kg equivalent to the adult dose (4 tablets/day), 50 mg/kg, and 100 mg/kg. It was then administered intraperitoneally (i.p.) at a volume of 0.1 ml/20 g-mouse. Fresh drug solutions were prepared on each day of experimentation. The control group received saline injections of the same volume and through the same routes of administration. All other chemicals were of the highest analytical grade.

(Antia)

Antia is a natural compound derived from a variety of mushrooms and plants, including the edible yamabushitake mushroom, the gotsukora and kothala himbutu plants, diosgenin (an extract from the tubers of dioscorea wild yam), and amla (Indian gooseberry). The ingredients are treated with an iron-based fluid called MRN-100. MRN-100 is made from phytosin and is an iron-based compound derived from bivalent and trivalent ferrates (hydroferrate fluid). The exact chemical composition of Antia is still under active investigation. Antia was provided by ACM Co., Ltd, Japan. Antia was prepared in distilled water (DW) with the concentration of MRN-100 at about $2\times10-12$ mol/L.

(Induction of SAD)

SAD was induced by ICV injection of STZ (3 mg/kg) into the lateral ventricle of mice according to the freehand procedure (38) and as updated by Warnock et al. to avoid the probability of cerebral vein penetration. After mice were anesthetized with thiopental (5 mg/kg, i.p.), the head was stabilized using downward pressure above the ears and the needle was inserted directly through the skin and skull into the lateral ventricle which was targeted by visualizing an equilateral triangle between the eyes and the center of the skull to locate the bregma, allowing the needle to be inserted about 1 mm lateral to this point. Mice behaved normally one minute following the injection.

(Experimental Design)

The experimental design is illustrated in FIG. 1. Mice were randomly divided into five groups, each containing 12 animals. Group I (Control): mice received ICV injection once and intraperitoneal (i.p.) saline injection for 21 consecutive days and served as normal control group. Group II (STZ): mice received STZ (3 mg/kg, ICV) once and served as a model for SAD. Group III (STZ+Antia 1): mice received STZ (3 mg/kg, ICV) followed by Antia (25 mg/kg, i.p) after five hours and then every day for 21 consecutive days. Group IV (STZ+Antia 2): mice received STZ (3 mg/kg, ICV) followed by Antia (50 mg/kg, i.p) after five hours and then every day for 21 consecutive days. Group V (STZ+Antia 3): mice received STZ (3 mg/kg, ICV) followed by Antia (100 mg/kg, i.p) after five hours and then every day for 21 consecutive days. Twenty-four hours after the end of the treatments, neurobehavioral tests were carried out, including object recognition and Morris water maze (MWM) tests, arranged in sequence from the least stressful test to the most stressful test. To minimize possible circadian variability, all testing was conducted during the animals' light cycle under top illumination.

(Behavioral Assessments)
Object Recognition Test.

The object recognition test is used to assess long-term memory and estimate cognition. In this study, the performed test took place on three consecutive days. On the first day (the habituation phase), each mouse was individually placed in a wooden box of dimensions 30×30×30 cm3 for 30 min in order to adapt to the surrounding environment. The second day was designated for the familiarization or training, where two wooden cubes identical in shape, color, and size were placed in opposite corners of the box, 2 cm from the walls. Each mouse was placed in the middle of the box and was left to explore these two objects for 10 min. On the third day, testing took place. One of the two identical cubes was replaced by a novel object that was different in shape, size, and color. Each mouse was exposed again to these two objects for 5 min. Objects added were cleaned with 70% ethanol between experiments with animals to ensure that the behavior was not guided by odor cues. All objects and locations were adjusted to decrease potential biases due to inclinations for particular locations or objects. A mouse could not displace the objects and the subjects were always placed into the box confronting the same wall. The animals' behavior was video-recorded and the following parameters were calculated:

1) Discrimination Index:

Difference in time exploring the novel and familiar objects divided by the total time spent exploring both objects. This result varies between +1 and −1, where a positive score indicates more time spent with the novel object, a negative score shows more time spent with the familiar object, and a zero score indicates a null preference.

2) Recognition Index:

Time spent by the animal exploring the novel object as a percentage of the total exploration time for both objects.

Morris Water Maze Test.

The MWM test is used to investigate spatial learning and memory in laboratory mice. The maze consisted of stainless-steel circular tanks (210 cm in diameter, 51 cm high) divided into four quadrants and filled with water (25±2° C.) to a depth of 35 cm. A submerged platform (10 cm width, 28 cm height), painted in black, was placed inside the target quadrant, 2 cm below the water surface. The platform was kept at a consistent position during the time of training and the test. A purple-colored non-toxic dye was added to make the water opaque so that the platform was made invisible. Memory-acquisition trials (120 s/trail) were performed two times a day for four consecutive days, with an interval of at least 15 min between the trials. During each acquisition trial, animals were left free to locate the hidden platform in the target quadrant. Once the mouse located the platform, it was left there for an additional 20 s to rest, while if an animal failed to reach the platform within 120 s, it was gently guided to the platform and kept there for 20 s. The mean escape latency was calculated as the time taken by each rat to find the hidden platform and was used as an index of acquisition or learning. On the fifth day, the mice were subjected to a probe-trial session where the platform was taken away from the pool and each rat was allowed to probe the pool for 60 s. The time spent by each rat in the target quadrant in which the hidden platform was previously placed was recorded as an indicator of retrieval or memory.

(Brain Processing)

After behavioral testing, mice were euthanized by cervical dislocation and brains were rapidly dissected and washed with ice-cold saline. The hippocampi (n=6) were excised from each brain on an ice-cold glass plate. The hippocampus was homogenized in ice-cold saline to prepare 10% homogenates that were divided into several aliquots and stored at −80° C. The other hippocampus was stored at −80° C. to be used for Western blot analysis.

(Biochemical Measurements)

Determination of oxidative stress and inflammatory biomarkers. Hippocampal lipid peroxidation was estimated by measuring the level of malondialdehyde (MDA). MDA was determined by measuring the thiobarbituric acid reactive substances according to the method described by Uchiyama and Mihara. Moreover, the brain glutathione (GSH) content was spectrophotometrically determined using Ellman's reagent according to the method described by Beutler et al. The results are expressed as M mol/mg protein.

Enzyme-Linked Immunosorbent Assay.

Hippocampal TNF-α and IL-6 levels were estimated using rat ELISA kits purchased from Ray Biotech Inc. (Norcross, Ga., USA) and R&D Systems Inc. (Minneapolis, USA), respectively. The procedures were performed according to the manufacturers' instructions. The results are presented as pg/mg protein for both TNF-α and IL-6.

Western Blot Analysis.

After protein solutions were extracted from the brain tissues, equal amounts of protein (20-30 μg of total protein) were separated by SDS-PAGE (10% acrylamide gel) and transferred to polyvinylidene difluoride membranes (Pierce, Rockford, Ill., USA) with a Bio-Rad Trans-Blot system. Immunodetection of Western blots was conducted by incubating the membranes at room temperature for 1 h with blocking solution comprised of 20 mM Tris-CI, pH 7.5, 150 mM NaCl, 0.1% Tween 20 and 3% bovine serum albumin. Membranes were incubated overnight at 4° C. with one of the following primary antibodies: P-JAK2 (Tyr 1007/1008), P-STAT3 (Tyr 705), IκB-α, GSK-3β, mTOR, COX-2, or β-actin, obtained from Thermo Fisher Scientific Inc. (Rockford, Ill., USA). After washing, peroxidase-labelled secondary antibodies were added and the membranes were incubated at room temperature for 1 h. The band intensity was analyzed using ChemiDoc™ imaging system with Image Lab™ software version 5.1 (Bio-Rad Laboratories Inc., Hercules, Calif., USA). The results are presented in arbitrary units after normalization to levels of the β-actin protein.

Determination of Protein Content.

Protein content was measured according to the method of Bradford. All the results are expressed as tissue concentration per mg protein.

(Statistical Analysis)

The data are presented as mean±S.E. Data were analyzed using one-way analysis of variance (ANOVA) followed by the Tukey-Kramer multiple comparison test. Graph Pad Prism software (version 6; Graph Pad Software, Inc., San Diego, Calif., USA) was used to perform the statistical analysis and create the graphical presentations. The level of significance was set to $p<0.05$ for all statistical tests.

(Results)

Figure 2A:
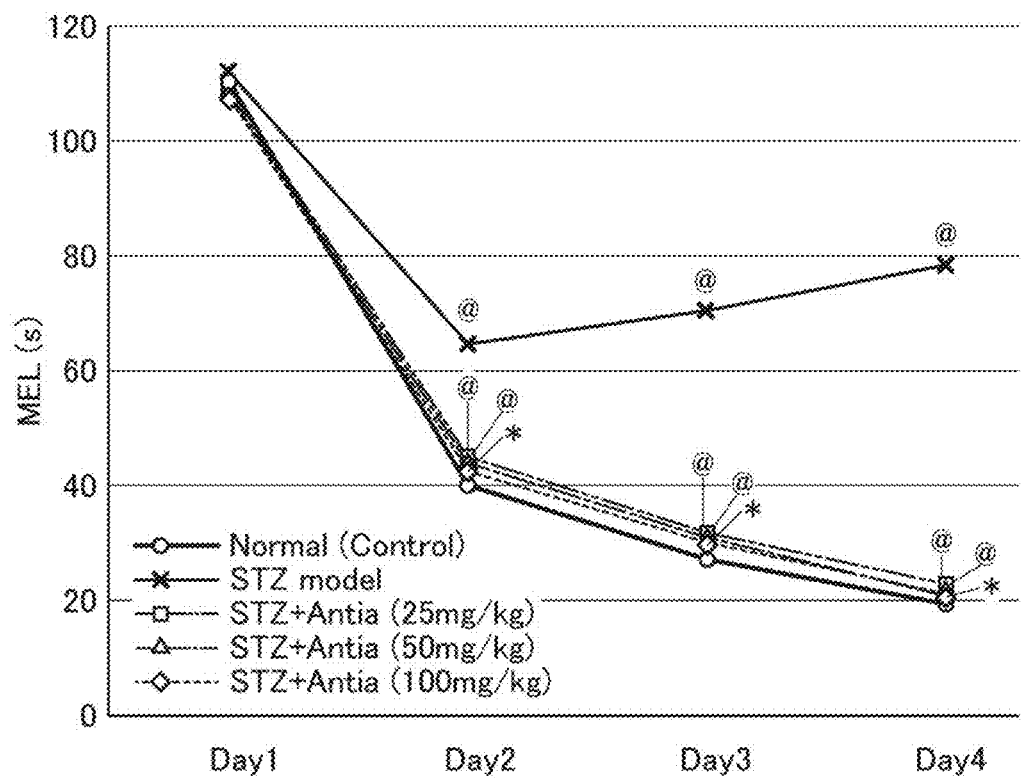
Figure 2B:
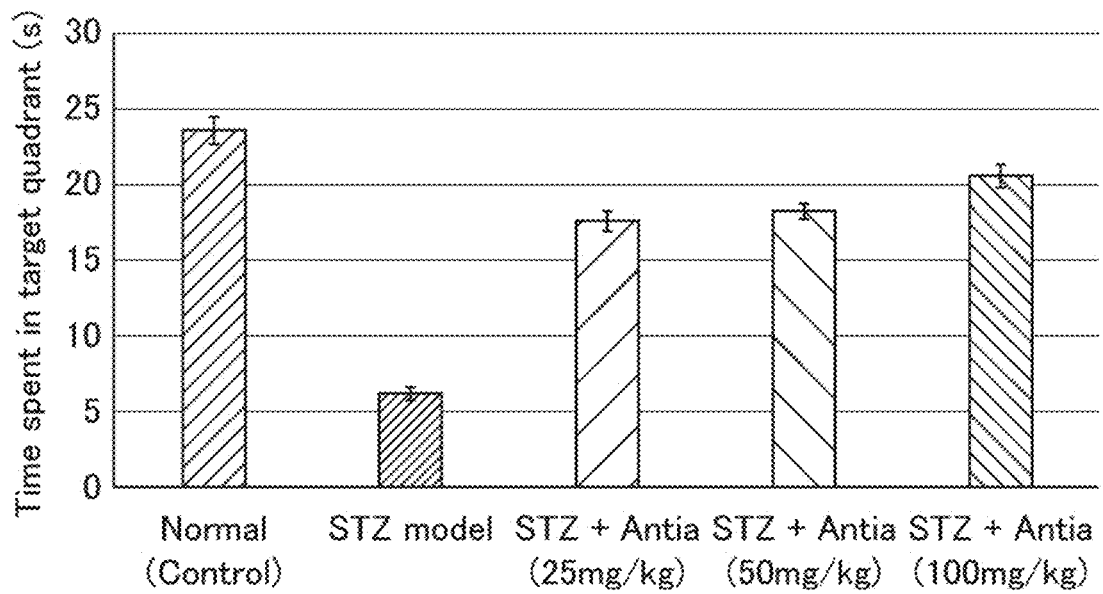

The effects of Antia on the behavioral and biochemical functions of ICV-STZ treated mice were measured with neurobehavioral tests and biochemical analysis of the hippocampal content. The effects of STZ and Antia (25, 50 and 100 mg/kg) on neurobehavioral tests were carried out within 24 h after the last day of Antia injection. The Morris water maze was used to examine the possible protective effect of Antia treatment on ICV-STZ injected mice. As illustrated in FIG. 2A for the mean escape latency (MEL), mice in different groups took different times to escape on day 2. Alzheimer's mice took 1.63 times as long to escape on day 2 as compared to control mice. On the other hand, Alzheimer's mice with Antia took only 1.08 times as long as control mice on day 2. These results were further confirmed in the subsequent days 3 and 4. The study of the effect of Antia on the time mice spent in the target quadrant of the Morris water maze (FIG. 2B) showed that Alzheimer's mice spent only 25.4% of the time in the quadrant as compared to control mice, while Alzheimer's mice with 25, 50, and 100 mg/kg of Antia spent 72.5%, 75.8%, and 85.4% of the time, respectively, as compared to control mice.

The effect of STZ and Antia was further examined through the discrimination and preference indices of the novel object recognition test. The discrimination index was decreased in STZ-induced SAD mice when compared to the control group, but it was significantly increased after Antia administration (25, 50, and 100 mg/kg) as compared to the STZ group in a dose dependent manner. In addition, the time spent exploring the novel object was lower in ICV-STZ injected mice by 63% compared to the control group, reflecting a lower preference index. Antia administration (25, 50 and 100 mg/kg) normalized the preference index, indicating that Antia-treated mice preferred the novel object over the familiar object in a dose dependent manner (FIG. 2C).

Figure 3A:
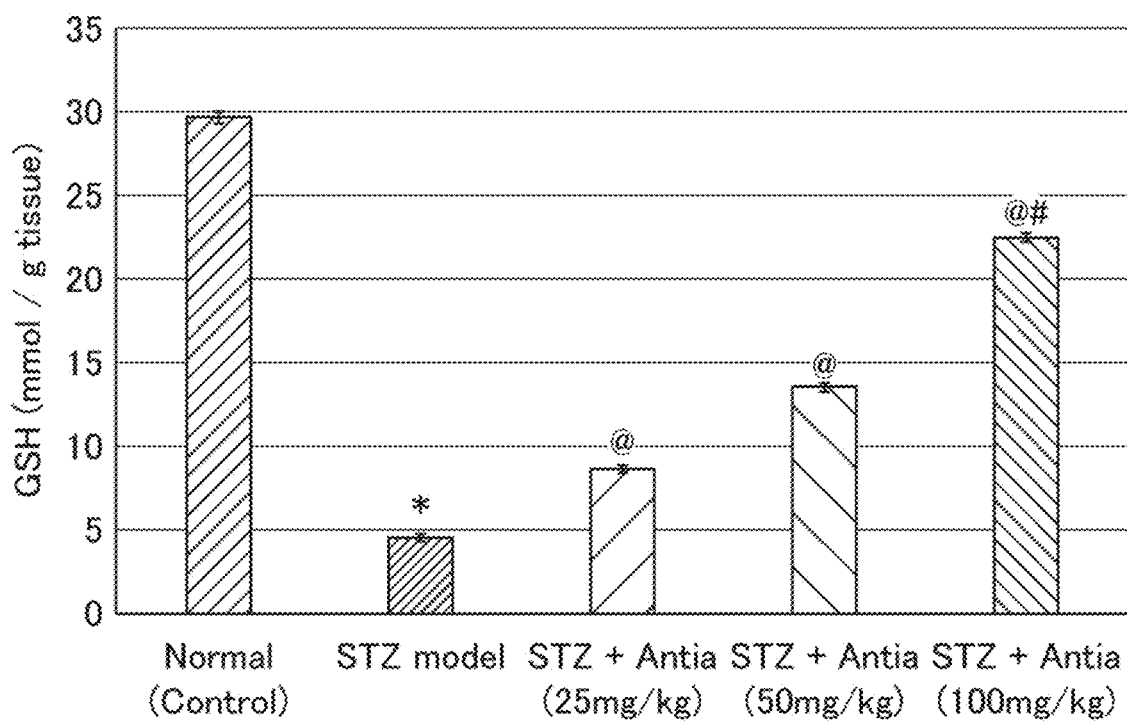
FIGS. 3A and 3B show the results of testing (2), indicating an effect of Antia on GSH and MDA hippocampal content in ICV-STZ injected mice, in which symbol * significantly different from normal group at $p<0.05$, symbol @ significantly different from ICV-STZ group at $p<0.05$, symbol # significantly different from Antia (25 mg/kg) at $p<0.05$, and symbol $ significantly different from Antia (50 mg/kg) at $p<0.05$.
Figure 3B:
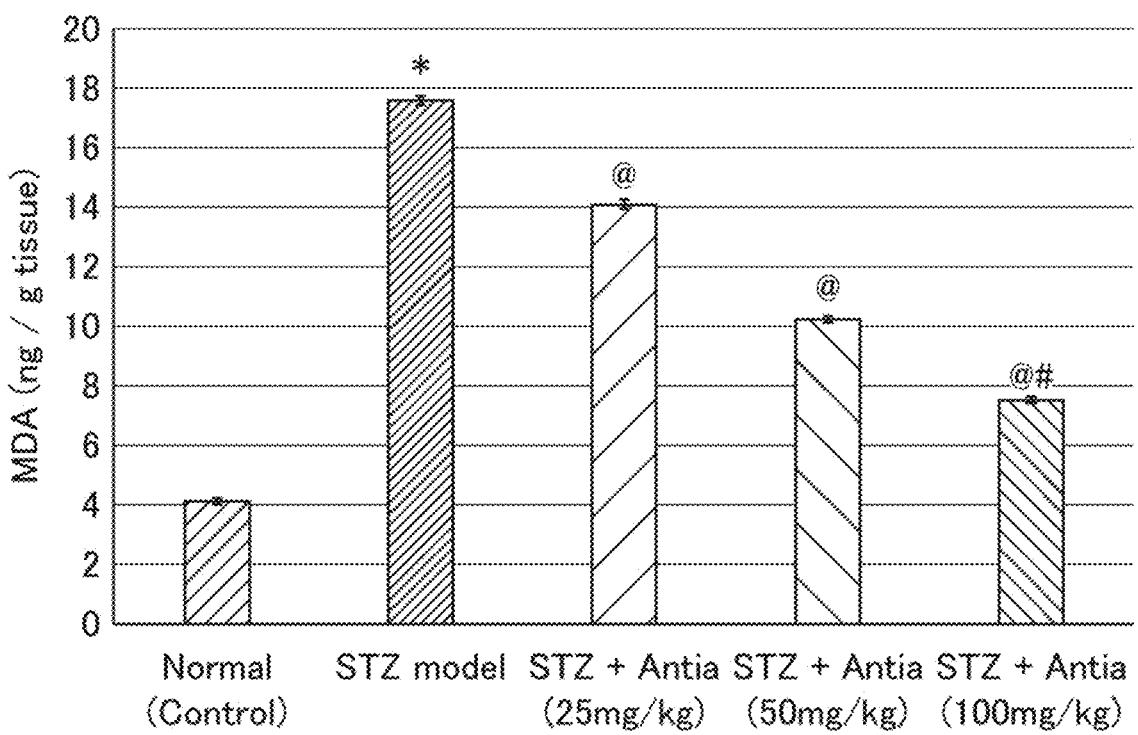

Several biochemical analyses of the hippocampal content in ICV-STZ treated mice were conducted in order to examine the ability of Antia to attenuate the amyloidogenic, inflammatory, autophagy and oxidative stress pathways. Studies on the protective effect of Antia treatments on the levels of glutathione (GSH) and malondialdehyde (MDA) hippocampal content were carried out. Results in FIG. 3A show that Alzheimer's mice had a GSH level that was 15.5% of the GSH level of control mice. On the other hand, Alzheimer's mice with Antia showed an elevation in the GSH content in a dose dependent manner that maximized at 78.7% of the control GSH level for 100 mg/kg Antia treatment. Results of the levels of MDA hippocampal content show significantly higher levels of MDA in ICV-STZ injected mice as compared with control mice by a factor of 4.3 fold. On the other hand, Alzheimer's mice with Antia showed an elevation in the MDA content of only 3.5 fold, 2.5 fold, and 1.8 fold for mice receiving Antia at doses of 25, 50 and 100 mg/kg respectively (FIG. 3B).

Figure 4:
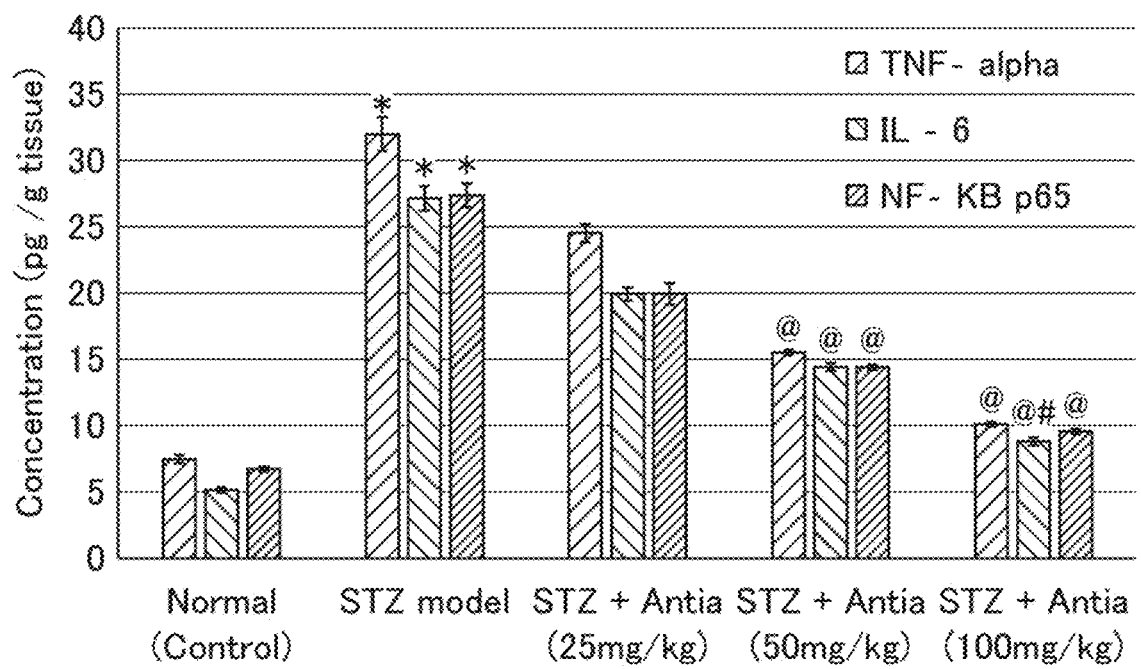
FIG. 4 shows the results of testing (3), indicating an effect of Antia on TNF-α and IL-6. NF-κB p65 hippocampal content in ICV-STZ injected mice, in which symbol * significantly different from normal group at $p<0.05$, symbol @ significantly different from ICV-STZ group at $p<0.05$, symbol # significantly different from Antia (25 mg/kg) at $p<0.05$, and symbol $ significantly different from Antia (50 mg/kg) at $p<0.05$.

The effect of ICV-STZ injection on the hippocampal content of anti-inflammatory cytokines was also examined in the presence and absence of Antia treatment. Two cytokines were examined: TNF-α and IL-6. Results in FIG. 4 show that STZ model mice exhibited a significant increase in the expression of TNF-α and IL-6 cytokines as compared with control mice, but treatment with Antia suppressed this induction in a dose dependent fashion that reached the level of control at 100 mg/kg. A similar trend can also be seen in the hippocampal content of NF-κB p65. Results in FIG. 4 show increased levels of NF-κB p65 in the Alzheimer's mice and its gradual decrease in Alzheimer's mice with Antia.

Figure 5:
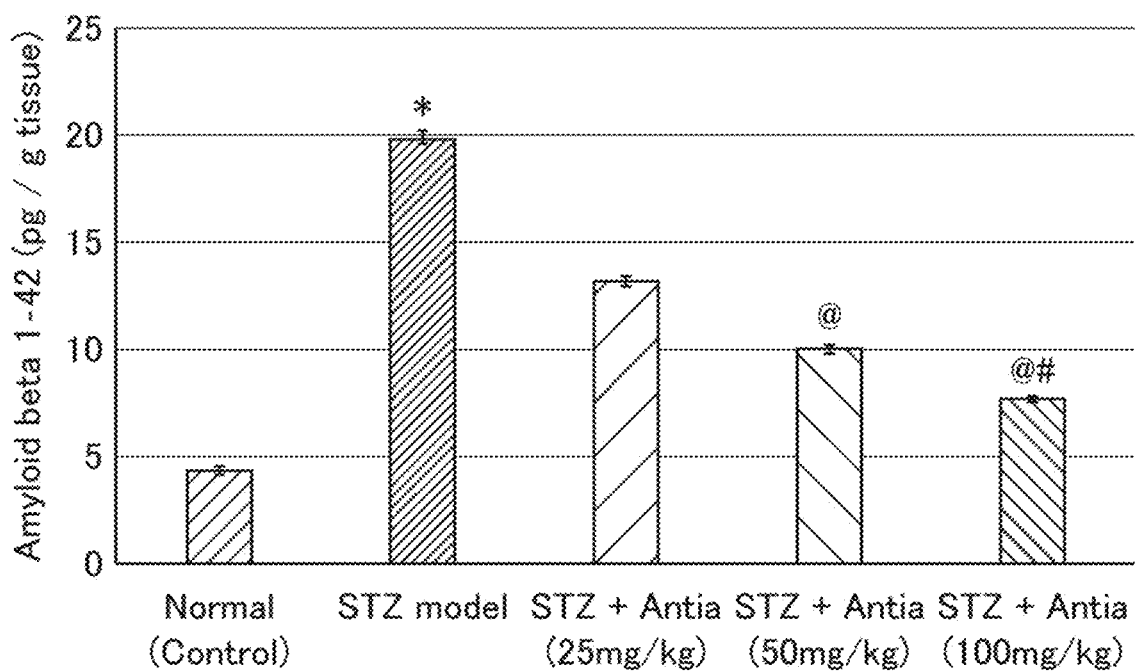
FIG. 5 shows the results of testing (4), indicating an effect of Antia on Amyloid $β_{1-42}$ hippocampal content in ICV-STZ injected mice, in which symbol * significantly different from normal group at $p<0.05$, symbol @ significantly different from ICV-STZ group at $p<0.05$, # significantly different from Antia (25 mg/kg) at $p<0.05$, and symbol $ significantly different from Antia (50 mg/kg) at $p<0.05$.

Since amyloid 1 makes up the plaques of Alzheimer's disease, where these normally solid proteins assemble into amyloid-like filaments, we examined the effect of Antia on Amyloid β1-42 hippocampal content in ICV-STZ injected mice. Results depicted in FIG. 5 show that STZ model mice exhibited an approximately 4 fold increase in the expression of amyloid β as compared with control mice. It is of interest to note that the levels of amyloid β were significantly decreased in Alzheimer's mice with Antia. The effect was dose dependent and reached its lowest levels at 100 mg/kg.

Figure 6A:
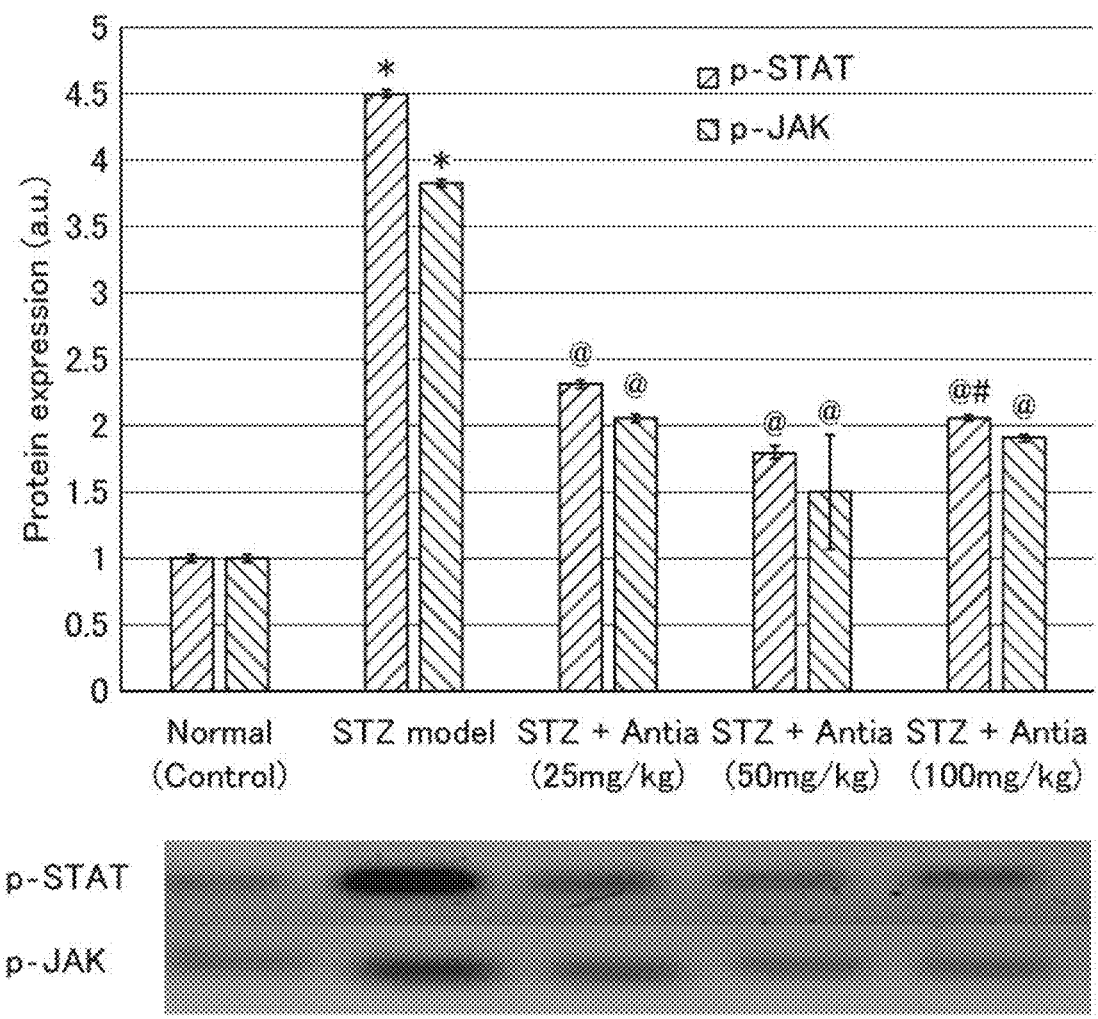

We further examined protein expression. The levels of phosphorylation of STAT and JAK protein expression is a well-established method used in Alzheimer's research. We examined whether treatment with Antia suppresses the phosphorylation of STAT expression in STZ mice. As expected, the levels of phosphorylation of STAT protein expression was significantly reduced as compared with control mice. However, treatment of STZ mice with Antia resulted in a significant inhibition in the phosphorylation level of STAT3 (FIG. 6A). A similar trend in results was observed with JAK2 protein expression. Treatment with Antia caused a significant inhibition in the phosphorylation level of JAK2 due to of STZ injection (FIG. 6A). These results indicate the protective effect of Antia for the JAK2/STAT3 pathway.

Earlier studies have shown that glycogen synthase kinase-3 (GSK-3) phosphorylates tau protein, the principal component of neurofibrillary tangles. Inhibition of GSK-3a offers anew approach to reduce the formation of both amyloid plaques and neurofibrillary tangles, two pathological hallmarks of Alzheimer's disease. Results in FIG. 6B show that Alzheimer's mice had a higher expression of GSK-3β level that was 7 fold larger than the GSK-3β level of control mice. On the other hand, treatment with Antia caused a dramatic inhibition in the expression of GSK-3β that was approximately 3 fold of the control. Results in FIG. 6B also show that Alzheimer's mice had a higher expression of IKB-α that approximately 6.5 fold larger than the IKB-α level of the control mice. On the other hand, treatment with Antia caused a dramatic inhibition in the expression of IKB-α that was approximately 2.8 fold of the control.

Several studies have shown that the mammalian target of rapamycin (mTOR) may play a role in amyloid @ and tau induced neurodegeneration. Earlier studies showed higher levels of mTOR phosphorylated at Ser2481 in the medial temporal cortex of AD cases compared to control cases.

Figure 6C:
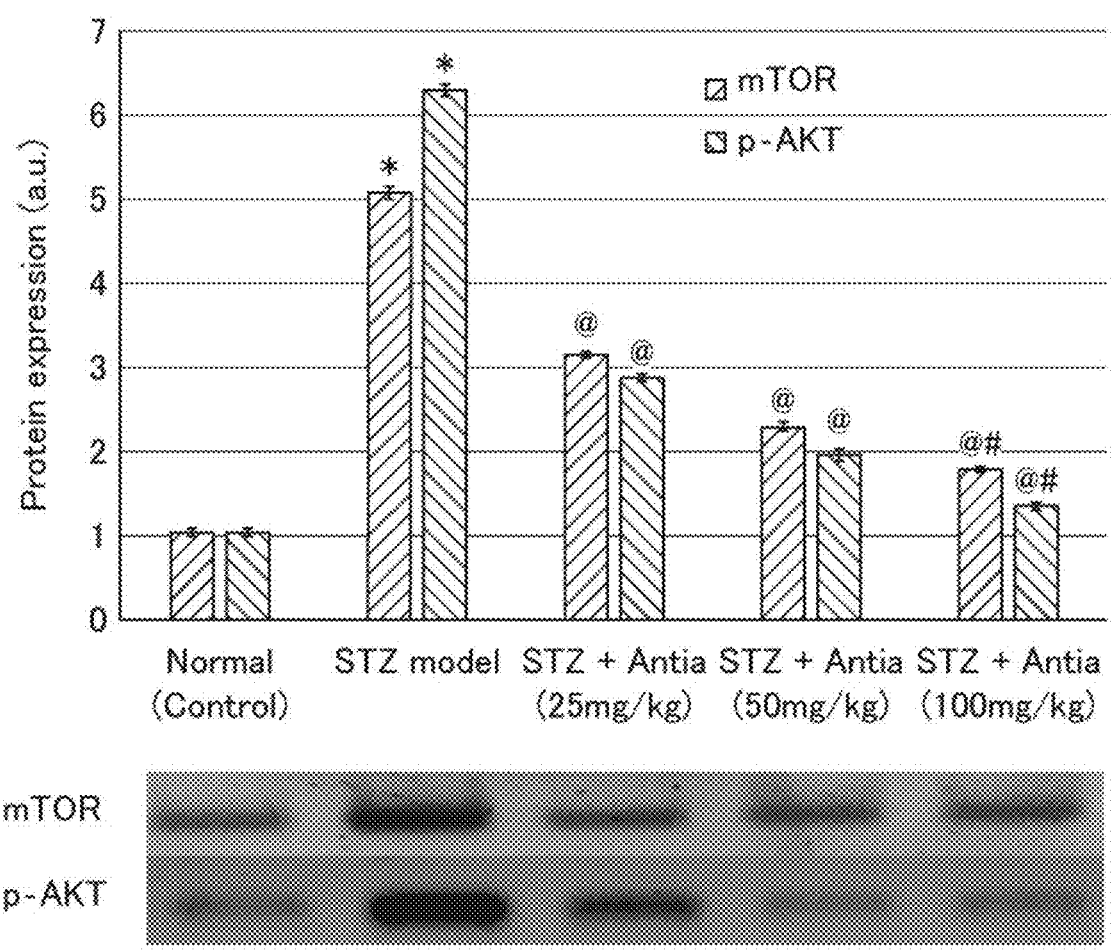

Results in FIG. 6C showed that STZ injected mice exhibited significantly increased levels of the mTOR and p-AKT protein expression that were 5× and 6× greater than the level of control mice, respectively, but treatment with Antia reversed that increase and brought it close to that of the control values.

Figure 6D:
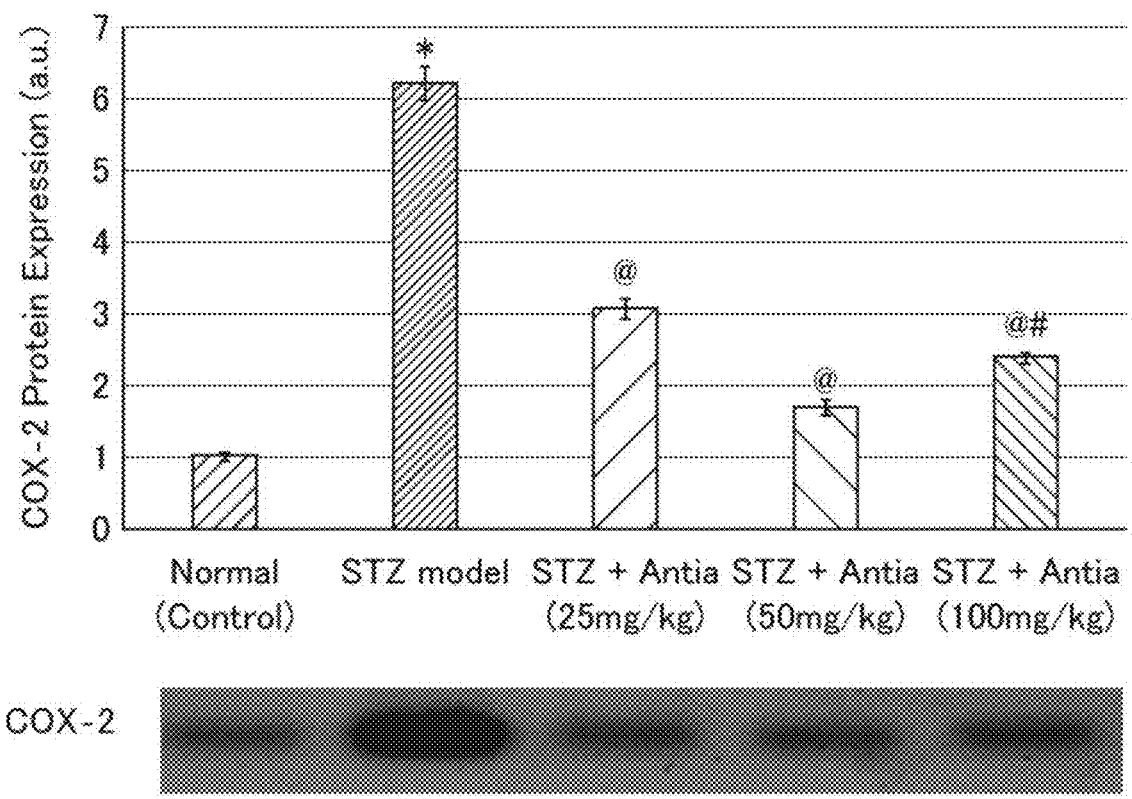

Finally, COX-2 is a key enzyme in the inflammatory processes. Results in FIG. 6D show that Alzheimer's mice exhibited a significant induction in COX-2 expression, 600% of the COX-2 level of control mice. Treatment with Antia, however, significantly reduced the expression of COX-2 to 150%-300%.

DISCUSSION

Results of the present study demonstrate the ability of the anti-oxidant Antia to exert a protective effect against SAD induced in mice. The constituents of Antia have previously been shown to possess various neuro-regenerative and protective properties. Yamabushitake mushrooms have been shown to synthesize nerve growth factor; gotsukora extracts reduce the amyloid β levels in the Alzheimer's-stricken brains of laboratory animals; diosgenin enhances the cognitive performance of mice; amla acts as a potent anti-oxidant with strong neuro-protective effects and cognitive enhancement properties; and kothala himbutu protects against deleterious cognitive changes in young diabetic rats and against mercury toxicity in mice hippocampi. Here, Antia is shown to attenuate cognitive dysfunction in the mouse model by targeting several linked pathways, including the amyloidogenic, inflammatory, autophagy, and oxidative stress pathways.

In the present study, induction of SAD in mice by STZ induced a significant cognitive decline in the Morris water maze and novel object recognition tests. ICV injection of STZ is an experimental model that mimics the progressive pathology of SAD similar to human brains. STZ-treated mice showed significant learning and memory deficits, as shown by the noticeable inability of mice to discriminate between familiar and novel objects in the Morris water maze and novel object recognition tasks. This is in harmony with previous studies. However, the profound elevation in escape latency during the acquisition trial and the time spent in the target quadrant during the probe trail in the Morris water maze test, as well as the increase in discrimination and preference indices in the novel object recognition test, proved that Antia prevented the STZ-induced impairments of spatial and short term memory. This improvement in the object recognition memory deficit could be attributed to the previously proven effects of several of Antia's ingredients. For example, it has been shown that diosgenin has an anti-amyloidogenic effect and that *Hericium erinaceus* has a strong neuroprotective effect against neuronal loss and dementia in AD. Furthermore, oral administration of dried yamabushitake mushroom powder has been demonstrated to be effective in improving mild cognitive impairment in humans.

STZ administration exhibited a significant increase in the expression of the hippocampal content of NF-κB and anti-inflammatory cytokines, namely TNF-α and IL-6. NF-κB plays a crucial role in the inflammatory responses in neurons where it induces the transcription of inflammatory target genes, including COX-2, IL-1β, IL-6, and TNF-α. TNF-α is involved in systemic inflammation, and in particular, it is involved in AD-related brain neuroinflammation as well as amyloidogenesis via β-secretase regulation. Moreover, profound neuropathological changes such as Parkinson's and Alzheimer's disease are associated with increased IL-6 expression in the brain. NF-κB has also been shown to regulate the BACE-1 expression level, the rate-limiting enzyme responsible for the production of amyloid β. The Janus Kinase/Signal Transducers and Activators of Transcription (JAK/STAT) signaling pathway emerged in the 1980s as the pathway mediating interferon signaling. Neuroinflammation is accompanied by diseases, and activation of the JAK2/STAT3 pathway leads to pathogenic inflammation. Thus, targeting the JAK2/STAT3 pathway can be used as a protective therapy for neuroinflammatory and neurodegenerative diseases such as AD.

In the present study, administration of Antia was shown to have a significant anti-inflammatory effect, as demonstrated by decreasing the levels of all measured inflammatory cytokines as well as dramatically inhibiting the expression of phosphorylated STAT3 and JAK2. The STAT3/JAK2 pathway has been linked to TNF-α production. The significant inhibition of TNF-α and NF-kB might be attributed to the action of *Hericium erinaceus*, known as yamabushitake, which has been shown to play an important role in transcriptional regulation of adhesion molecules and numerous cytokines including IL-6 and TNF-α.

Neuroinflammation has been linked to a deficit of autophagy, which may contribute to neurodegeneration. The mammalian target of rapamycin (mTOR) is known to regulate autophagy, along with protein kinase B (Akt). Several studies emphasize the close relationship between mTOR signaling and the presence of amyloid β plaques and cognitive impairment in AD. Furthermore, in human and rat studies of AD, autophagy activation has been linked to GSK-3β inhibitors and its deficit has been found to contribute to the pathological accumulation of tau aggregates.

Treatment with Antia reversed the elevated expression of mTOR, Akt, IKB-α, and GSK-3β levels after STZ injection and brought it to closer that of the control. Recent reports showed that increasing the axonal density of neurons by diosgenin caused a significant improvement in cognitive function. This could be achieved through modulation of the PI3K-Akt pathway, which is known to regulate local protein translation via the mTOR pathway, thus playing an important role in axon regeneration.

Results of this study showed that Antia increases GSH and decreases lipid peroxidation in STZ-treated mice. Previous research showed that the generation of ROS via amyloid β during self-aggregation may damage neurons and cause neuronal death. Lipid peroxidation is considered to be one of the major outcomes of free radical-mediated injury that directly damages membranes, and increased lipid peroxidation has been reported in the brain of AD patients. Treatment of STZ-treated mice with Antia improved the oxidative stress parameters. This might be attributed to its previously known ability to reverse oxidative-stress-induced mitochondrial dysfunction and apoptosis. In addition, *Centella asiatica*, commonly known as gotsukora, has been found previously to exhibit noticeable free radical scavenging properties, decreased lipid peroxidation, and protection from DNA fragmentation due to oxidative stress, providing multiple mechanisms to alter pathology in Alzheimer's brain. Previous studies have shown the beneficial antioxidant properties of MRN-100, the hydroferrate fluid that is used to treat Antia's constituents, to increase brain levels of GSH, superoxide dismutase, catalase, and glutathione peroxidase and to inhibit of the levels of oxidative stress biomarkers including MDA, nitric oxide, and total free radicals. GSH is an anti-oxidant that has the ability to prevent damage caused by ROS and may protect against oxidative and neurotoxic degeneration of oligometric amyloid.

CONCLUSIONS

It could be concluded from the present study that Antia exerts a significant protection against sporadic AD induced by ICV injection of STZ. This effect is achieved through targeting the amyloidogenic, inflammatory, and oxidative stress pathways. The JAK2/STAT3 pathway played a protective role for the induced neuroinflammation, which is mediated through modulation of the Akt/mTOR/GSK-3β pathway. To our knowledge, this is the first work done to investigate the protective effect of Antia against neurodegenerative diseases such as SAD.

The invention claimed is:

1. A composition comprising extracts obtained from each of *Centella asiatica* (gotu kola), Phyllanthus emblica (amla), *Salacia reticulata* (kotarahinbutsu) and *Hericium erinaceus* (yamabushitake), diosgenin and a divalent/trivalent iron salt, all in effective amounts, wherein said extract of gotu kola comprises about 20.0 to about 28% by weight of said composition, said extract of amla comprises about 13.0 to about 18.0% by weight of said composition, said extract of kotarahinbutsu comprises about 20.0 to about 26.0% by weight of said composition, said extract of yamabushitake comprises about 10.0% to about 15.0% by weight of said composition, said diosgenin comprises about 20.0 to about 26.0% by weight of said composition and said divalent/trivalent iron salt comprises about 1.5% to about 4% by weight of said composition and wherein said divalent/trivalent iron salt is prepared from one of ferric chloride, ferric sulfate, or ferric nitrate.

2. The composition as claimed in claim 1, which is effective for the prevention and/or treatment of cognitive impairment in a subject or patient.

3. The composition as claimed in claim 1, further comprising an effective amount of zinc.

4. The composition as claimed in claim 2, further comprising an effective amount of.

5. The composition according to claim 3 wherein said zinc comprises about 0.5% to about 1.5% by weight of said composition.

6. The composition according to claim 4 wherein said zinc comprises about 0.5% to about 1.5% by weight of said composition.

* * * * *